United States Patent [19]

Benson

[11] 4,199,533

[45] Apr. 22, 1980

[54] CONVERSION OF METHANE

[75] Inventor: Sidney W. Benson, Palos Verdes Estates, Calif.

[73] Assignee: University of Southern California, Los Angeles, Calif.

[21] Appl. No.: 957,385

[22] Filed: Nov. 3, 1978

[51] Int. Cl.$^2$ .................. C07C 9/06; C07C 11/04
[52] U.S. Cl. .................. 585/500; 585/657; 423/486; 585/700
[58] Field of Search ......... 260/676 R, 677 R, 677 XA

[56] References Cited

U.S. PATENT DOCUMENTS

| | | | |
|---|---|---|---|
| 1,298,929 | 4/1919 | Graul et al. | 260/676 R |
| 1,677,363 | 7/1928 | Olivier | 260/683 R |
| 2,063,133 | 12/1936 | Tropsch | 196/10 |
| 2,065,323 | 12/1936 | Thomas et al. | 196/52 |
| 2,488,083 | 11/1949 | Gorin et al. | 260/677 |
| 2,700,594 | 1/1955 | Bills | 260/683 R |
| 3,349,120 | 10/1967 | Lusman | 260/505 |
| 3,429,939 | 2/1969 | Yildirim et al. | 260/654 |
| 4,051,193 | 9/1977 | Kurtz et al. | 260/683.3 |

OTHER PUBLICATIONS

Jones et al., Chem. Abstracts 15 (1921), p. 1983c.
Pritchard et al., J. Am. Chem. Soc. 77 (1955), pp. 2629–2633.

*Primary Examiner*—Arthur P. Demers
*Attorney, Agent, or Firm*—Nilsson, Robbins, Dalgarn, Berliner, Carson & Wurst

[57] ABSTRACT

A method for chemically converting methane gas into higher molecular weight hydrocarbons by using chlorine gas as a recyclable, active catalyst.

12 Claims, 1 Drawing Figure

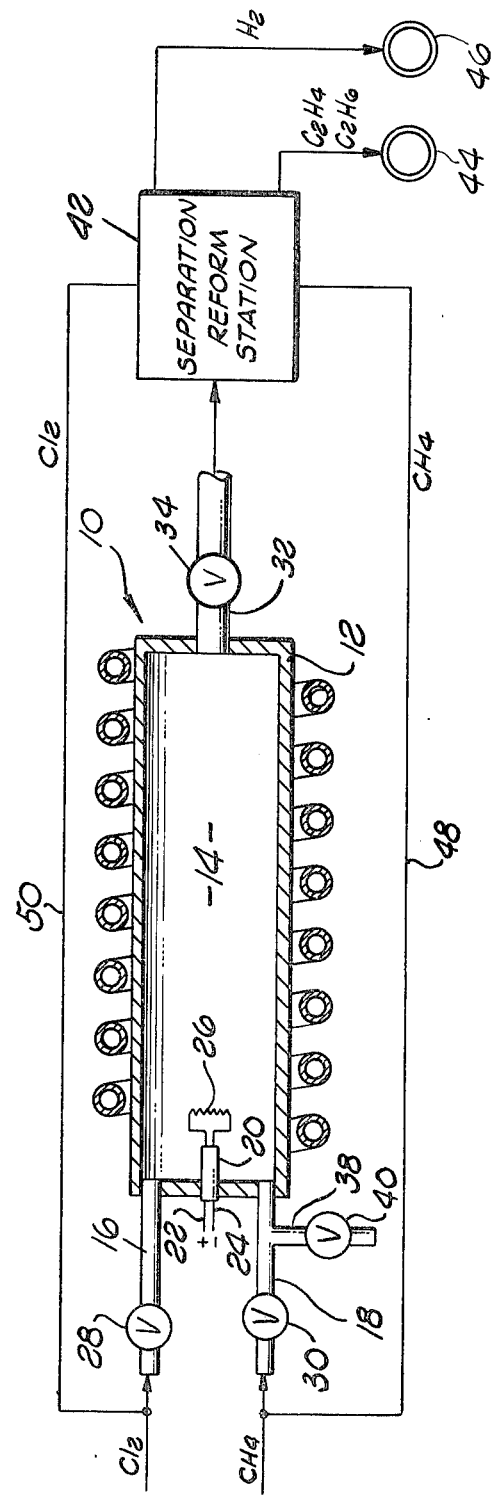

CONVERSION OF METHANE

FIELD OF THE INVENTION

The field of art to which the invention pertains includes the field of methane conversion to higher molecular weight hydrocarbons.

BACKGROUND AND SUMMARY OF THE INVENTION

Methane is available in great quantities in natural gas. The composition of natural gas varies with the source but essentially it is made up of methane (typically about 75% by weight), ethane, propane, and other paraffinic hydrocarbons, along with small amounts of inorganic gases. The chief use of methane is as a fuel, but processes are known for converting it to higher molecular weight products. For example, methane can be first converted to methyl halide and then catalytically condensed to hydrocarbons having two or more carbon atoms to the molecule. Such a process is described in Gorin et al U.S. Pat. No. 2,488,083. Modern processes convert methane to ethylene, acetylene, hydrogen and high surface area carbon by high temperature pyrolysis. Carbon produced by the process, although economically valuable, presents costly and sometimes difficult handling and disposal problems. If the methane could be converted to primarily gaseous or liquid materials, conversion could be accomplished at the well site so that one could ship product rather than methane. Shipment from the well site would therefore be less hazardous, less costly and have higher value. By converting the methane to ethane, and/or ethylene, it would have great value as a petrochemical feedstock for the production of ethylene oxide, ethylbenzene, ethylchloride, ethylene dichloride, ethyl alcohol and polyethylene from which are manufactured hundreds of end products.

The present invention provides a process for the conversion of methane to saturated and unsaturated hydrocarbons. It is a one-step process using chlorine gas as a recyclable, active catalyst and is simple, economical and readily usable at the well site. It can be operated so as to produce a desired mix of the hydrocarbons and can also produce hydrogen.

Specifically, a method is provided for converting methane into at least one higher molecular weight hydrocarbon, which method comprises reacting a mixture of chlorine and a gas comprising methane in specific ratios and under specific temperature conditions. In particular, the methane and chlorine is used in a mole ratio of about 1:1 to 10:1 under conditions to provide a reaction temperature of at least 700° C., preferably 700°–1710° C. The result is the formation of hydrogen chloride with varying quanitities of hydrogen and saturated and unsaturated hydrocarbons, notably ethane and ethylene.

The methane and chlorine gases are mixed together and ignited in a reaction vessel. The composition of the resultant product can be controlled by varying the ratio of the reactants, the temperature and/or the pressure within the reaction vessel. While small amounts of higher homologues can also be produced, with regard to the production of ethane, ethylene and hydrogen, the reaction proceeds in accordance with the general equation:

$$2CH_4 + (1+y)Cl_2 \rightarrow (2y+2)HCl + (1-x)C_2H_6 + xC_2H_4 + (x-y)H_2$$

wherein x is from 0 to 1, y is from 0 to 1 and x is greater than y. Again, with regard to the production of ethane and ethylene, when y is 0 the process is stoichiometric with respect to methane consumption and it is preferred to operate the process with a mole ratio of methane to chlorine of at least 2:1. This gives rise to the simplified equation:

$$2CH_4 + Cl_2 \rightarrow 2HCl + (1-x)C_2H_6 + xC_2H_4 + xH_2$$

wherein x is from 0 to 1.

By operating with at least a stoichiometric ratio of methane to chlorine, one avoids the danger of contamination with polychlorinated end product. An inspection of the above formula reveals that the main products of the reaction will vary and include ethylene, hydrogen and ethylene, ethane, and mixtures thereof. The value of x, i.e., the composition of the product, can be controlled by controlling the pressure within the reaction vessel and the temperature of reaction. The temperature in turn can be controlled by increasing the relative amount of methane mixed with the chlorine, or by adding water to the reaction mixture, or physically by external cooling of the reaction chamber. The pressure can be controlled by appropriate valving of reactant and product streams or by allowing the mixture to do recoverable work such as by expansion.

Using well known methods, the hydrogen, hydrogen chloride and excess methane can be separated from the other products. The methane can be recycled or it and the hydrogen can be used to provide energy for the system. Hydrogen of course can also be shipped for use in other processes. The hydrogen chloride can be burned in air to reform the initial chlorine which can then be recycled to constitute the reaction mixture.

BRIEF DESCRIPTION OF THE DRAWING

The accompanying drawing illustrates the present process schematically and by way of example including an apparatus suitable for carrying out the process according to this invention.

DETAILED DESCRIPTION

As required, a detailed illustrative embodiment of the invention is disclosed herein. However, it is to be understood that this embodiment merely exemplifies the invention which may take forms that are different from the specific illustrative embodiment disclosed. Therefore, specific structural and functional details are not to be interpreted as necessarily limiting, but as a basis for the claims which define the scope of the invention.

In operating the process, chlorine and methane are introduced at one side of an elongated reaction chamber and are ignited upon contact. A rapid exothermic reaction occurs producing a flame. With a mole ratio of methane to chlorine of about 2:1, about 24 kcal/mole $Cl_2$ is released producing an adiabatic flame temperature of about 1530° C., starting at room temperature.

More specifically, referring to the accompanying drawing, a reactor 10 is provided including a gas-impervious casing 12 which defines an inner elongated reaction zone 14. Chlorine reactant and hydrogen chloride product are both corrosive gases, particularly at high temperatures. Therefore, the reactor casing 12 should be coated internally with ceramic such as alundum ($Al_2O_3$), silica, or the like, or with metallic carbides, borides or nitrides. The reactor 10 includes at one end a first gas inlet conduit 16 for introducing chlorine into the reaction zone 14, and a second gas inlet 18 conduit for introducing gas comprising methane. A bushing 20 is inserted through the reactor wall at that end through which extend electrically conducting wires 22 and 24 connected to a high resistance wire 26 within the reaction zone 14 at the confluence at the chlorine and methane streams. Alternatively, one can use a spark coil. The gas inlet conduits 16 and 18 are provided with flow metering valves 28 and 30, respectively, for controlling the flow of chlorine and methane gas, respectively. The opposite end of the reactor 12 is formed with an outlet means 32 for withdrawing product gases from the reactor and it is fitted with a metering valve 34. Heat exchange means are provided for controlling the temperature within the reaction zone 14 comprising, in this case, cooling coils 36 through which flow the refrigerant fluid (not shown). Alternatively, one could dispose electrical heating coils around the reactor casing 12 to provide an increased temperature. A quench liquid inlet conduit 38 is connected into the methane inlet conduit 18, downstream of its metering valve 30 and is provided with a control valve 40. Water can be optionally inserted through the quench inlet conduit 38 to control the temperature in the reaction zone 14.

Also illustrated in the drawing is a separation/reform station 42 for fractionation of the hydrocarbon and hydrogen product and reformation of the hydrogen chloride, as well as conduits 44 and 46 for conveying hydrocarbon and hydrogen, respectively, to storage.

In operation, metered quantities of chlorine and methane are introduced into the reaction zone 14 through the inlet conduits 16 and 18. Current is supplied to the electrically conducting wires 22 and 24 so that the high resistance wire 26 glows sufficiently to ignite the mixture of chlorine and methane at their confluence (or a spark can be formed by any means). In the reaction zone 14, there occurs a rapid exothermic reaction between the methane and chlorine producing a flame with an adiabatic flame temperature which varies depending upon the ratio of methane to chlorine. The flame zone is measured in millimeters, the reaction proceeding through the flame in milliseconds. In an exemplification, the mole ratio of methane to chlorine is about 2:1 resulting in an adiabatic flame temperature of about 1530° C.

The reaction produces hydrogen chloride, hydrogen and, as hydrocarbons, primarily ethane and ethylene although higher molecular weight hydrocarbons can also be produced in small quantities. With respect to the production of ethane and ethylene, at the stoichiometric mole ratio of methane to chlorine, or with higher amounts of methane, the reaction proceeds generally in accordance with the equation:

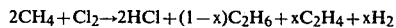

wherein x is from 0 to 1. The value of x is determined by the temperature of the reaction and the pressure within the reaction vessel, increasing with higher temperatures and with lower pressures. Accordingly, with the higher temperatures within the preferred range given above, and atmospheric pressure or lower, the reaction proceeds to produce ethylene and hydrogen to the substantial exclusion of ethane. On the other hand, at the lower temperatures, obtainable for example with excess methane which serves to lower the temperature, the reaction proceeds to produce ethane to the substantial exclusion of ethylene and hydrogen. Temperature can be controlled not only by excess methane, but also by cooling of the reactor casing 12 via flow of refrigerant through the cooling coils 36, or by introducing metered quantities of water through the quench conduit 38.

When the mole ratio of methane to chlorine is stoichiometric, i.e., 2:1, or thereabouts, substantial quantities of each of ethane, ethylene and hydrogen are produced along with hydrogen chloride. At high ratios of methane to chlorine, for example at a mole ratio of 10:1, the value of x approaches 0 so that ethane is produced to the substantial exclusion of ethylene and hydrogen. When chlorine is added in excess of stoichiometric, for example at a mole ratio of 1:1, the value of x approaches 1 so that ethylene and hydrogen are produced to the substantial exclusion of ethane. Of course, under these latter conditions, hydrogen produced would react with the excess chlorine to yield additional amounts of hydrogen chloride. Accordingly, over the complete range of mole ratios of methane to chlorine of 1:1 to 10:1, the reactions can be described with the general equation:

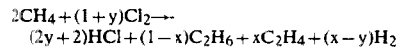

wherein x is from 0 to 1, y is from 0 to 1 and x is greater than y.

Preferably, the reaction is conducted to withdraw product so as to maintain a pressure that is approximately atmospheric. However, somewhat lower than atmospheric pressures can be used by associating a pump with the outlet conduit 32. In such case, the relative amounts of ethylene and hydrogen would be increased consequently decreasing the amount of ethane. On the other hand, superatmospheric pressure can be used by appropriate control of the outlet valve 34 in conjunction with appropriate control of the inlet valves 28 and 30. In such case, the relative amount of ethane would be increased with consequent decrease in the amounts of ethylene and hydrogen.

Using the above procedure, the time for reaction is very fast being accomplished in fractions of a second, and no catalyst is needed. Oxygen is not needed, but a small amount can be tolerated so that there is no need to purge the reactor prior to use.

As feed material, one can use methane alone or as found in natural gas. In the latter case, the higher molecular weight components of the natural gas for the most part feed through as excess hydrocarbon and are recovered along with the synthesized ethane and ethylene. The products of the reaction are separated and recovered at the separation station 42. Methods and apparatus for separating hydrogen, methane and hydrogen chloride from ethane, ethylene and the like are well known. For example, one can refer to Gorin et al U.S. Pat. No. 2,488,083. A fractionator can be used to operate as a stripping column for the removal of light gases from the reaction product. The most volatile of the gases, namely hydrogen, is led over a line through the conduit 46 for delivery to a storage tank. Methane is recycled along the line 48 into the second gas inlet conduit 18 to constitute the reaction mixture.

In a particular fractionation procedure, the methane ethylene, ethane and hydrogen chloride can be delivered together to a condensor. Overhead gas consisting primarily of methane can then be recycled as above. The remaining product containing the remaining hydrocarbons and hydrogen chloride may be treated to separate hydrogen chloride from the remaining gases by any means well known in the art, such as by absorption on zeolites, or with a water wash. The remaining hydrocarbons can then be delivered to the conduit 44 for conveyance to a storage tank.

The hydrogen chloride can be burned in air to reform the initial chlorine, in accordance with the reaction:

$$2HCl + \tfrac{1}{2}O_2 \rightarrow Cl_2 + H_2O$$

and can be done catalytically at relatively low temperatures. This reaction is also exothermic and can provide recoverable heats and high flame temperature if carried out in the flame. The chlorine from the foregoing reaction is delivered over the line 50 to the first gas inlet conduit 16 to constitute the reaction mixture.

The following examples will further illustrate the invention.

EXAMPLE 1

Using the apparatus shown in the accompanying drawing, chlorine is reacted with natural gas containing 78% methane, 13% ethane, 6% propane, 1.7% butane and small amounts of paraffinic hydrocarbons and inorganic gases. An amount of natural gas is used so that the mole ratio of hydrocarbon to chlorine is 2:1. The reaction is started and continued to yield product through the outlet conduit of the reactor at a rate which maintains a pressure within the reactor of about atmospheric pressure. A flame will be produced having an adiabatic flame temperature of about 1530° C. yielding a mixture as product consisting principally of hydrogen, hydrogen chloride, ethane, ethylene and some excess methane.

EXAMPLE 2

The procedure of Example 1 is followed but the amount of natural gas is controlled so that the mole ratio of hydrocarbon to chlorine is 1:1. The reaction is conducted at about 1710° C. with the production of ethylene to the substantial exclusion of ethane.

EXAMPLE 3

The procedure of Example 1 is followed except that the natural gas is provided in an amount sufficient to provide a mole ratio of hydrocarbon to chlorine of 10:1. Additionally, refrigerant is supplied to the cooling coils so that the reaction takes place at 700° C., resulting in product containing ethane to the substantial exclusion of ethylene and hydrogen.

In brief review, it will be seen that a process has been provided which in result requires simply the delivery of methane or natural gas to the reactor along with make-up amounts of chlorine (resulting simply from process losses) and obtaining ethane, ethylene and hydrogen as products. The process is simple to conduct, economical and efficient and is capable of being constructed at the well site so that instead shipping methane, ethane and ethylene itself can be shipped with less hazard, less cost and with higher value. Alternatively, well known thermal or catalytic processes can be used to further condense the $C_2H_4$ to $C_4$, $C_6$, $C_8$ or higher homologues.

I claim:

1. A method for converting methane into at least one higher molecular weight hydrocarbon, which comprises reacting a mixture of chlorine and a gas comprising methane in a mole ratio of methane to chlorine to about 1:1 to 10:1 under conditions to provide a reaction temperature of at least 700° C. and to form as products hydrogen chloride and hydrocarbon selected from ethane, ethylene, and mixtures thereof.

2. The method of claim 1 in which said chlorine and methane are reacted by igniting said mixture.

3. The method of claim 1 in which said temperature is in the range of 700° C.–1710° C.

4. The method of claim 1 in which said reaction proceeds in accordance with the equation $$2CH_4 + (1+y)Cl_2 \rightarrow (2y+2)HCl + (1-x)C_2H_6 + xC_2H_4 + (x-y)H_2$$

wherein x is from 0 to 1, y is from 0 to 1 and x is greater than y.

5. The method of claim 1 in which the mole ratio of methane to chlorine is at least 2:1.

6. The method of claim 5 in which said reaction proceeds in accordance with the equation:

$$2CH_4 + Cl_2 \rightarrow 2HCl + (1-x)C_2H_6 + xC_2H_4 + xH_2$$

wherein x is from 0 to 1.

7. The method of claim 1 in which the mole ratio of methane to chlorine is greater than 2:1 whereby to obtain methane in mixture with said products, and including the step of separating methane from said products and recycling said separated methane to constitute said mixture.

8. The method of claim 1 including the step of reforming chlorine from said hydrogen chloride and recycling said reformed chlorine to constitute said mixture.

9. The method of claim 1 conducted at about atmospheric pressure.

10. A method for converting methane into at least one higher molecular weight hydrocarbon, which comprises igniting a mixture of chlorine and a gas comprising methane in a mole ratio of methane to chlorine of 1:1 to 10:1 under conditions to provide a reaction temperature in the range of 700°–1710° C. and to produce hydrogen chloride and other products selected from (a) ethylene, (b) hydrogen and ethylene, (c) ethane, and (d) mixtures thereof.

11. The method of claim 10 in which the mole ratio of methane to chlorine is at least 2:1.

12. The method of claim 10 conducted at about atmospheric pressure.

* * * * *